(12) United States Patent
Nakayama et al.

(10) Patent No.: US 6,960,672 B2
(45) Date of Patent: Nov. 1, 2005

(54) PROCESSES FOR PRODUCING ALKYL ESTER OF FATTY ACID

(75) Inventors: Masahide Nakayama, Kyoto (JP); Keiichi Tsuto, Kyoto (JP); Takenori Hirano, Kagoshima (JP); Tsutomu Sakai, Kyoto (JP); Ayato Kawashima, Kyoto (JP); Hirohisa Kitagawa, Kyoto (JP)

(73) Assignee: Revo International Inc., Kyoto (JP)

(*) Notice: Subject to any disclaimer, the term of this patent is extended or adjusted under 35 U.S.C. 154(b) by 0 days.

(21) Appl. No.: 10/473,252

(22) PCT Filed: Mar. 28, 2002

(86) PCT No.: PCT/JP02/03039
§ 371 (c)(1),
(2), (4) Date: Sep. 29, 2003

(87) PCT Pub. No.: WO02/081607
PCT Pub. Date: Oct. 17, 2002

(65) Prior Publication Data
US 2004/0087809 A1 May 6, 2004

(30) Foreign Application Priority Data

Mar. 30, 2001 (JP) ......................................... 2001-97889
Apr. 12, 2001 (JP) ....................................... 2001-114325

(51) Int. Cl.$^7$ .............................................. C11C 3/00
(52) U.S. Cl. ...................................................... 554/169
(58) Field of Search ......................................... 554/169

(56) References Cited

U.S. PATENT DOCUMENTS 5,350,879 A 9/1994 Engel et al.
6,090,959 A * 7/2000 Hirano et al. ............... 554/169

FOREIGN PATENT DOCUMENTS

| EP | 0 535 290 A1 | 4/1993 |
|---|---|---|
| EP | 985654 A1 | 3/2000 |
| EP | 1061120 A1 | 12/2000 |
| EP | 1126011 A2 | 8/2001 |
| JP | 61-14044 A | 1/1986 |
| JP | 62-218495 A | 9/1987 |
| JP | 6-313188 A | 11/1994 |
| JP | 7-197047 A | 8/1995 |
| JP | 7-310090 A | 11/1995 |
| JP | 11-179203 A | 7/1999 |
| JP | 2000-44984 A | 2/2000 |
| JP | 2000-204392 A | 7/2000 |

OTHER PUBLICATIONS

Udo R. Kreutzer, JAOCS, vol. 61, No. 2. 343–348, Feb. 1984.
Sungunan et al., React. Kinet. Catal. Letters, vol. 62, No. 2, pp. 327–332 (1997).
Peterson et al., *Journal of the American Oil Chemists' Society*, 61:1593–1597 (1984).
Saka et al., *Biomass, Proc. Biomass Conf. Am.*, 1: 797–801 (1999).
Peterson et al., JAOCS, vo. 61, pp. 1593–1597, 1984.*

* cited by examiner

*Primary Examiner*—Deborah D. Carr
(74) *Attorney, Agent, or Firm*—Birch, Stewart, Kolasch & Birch, LLP

(57) ABSTRACT

The present invention relates to a process for preparing an alkyl ester of a fatty acid wherein a transesterification reaction is carried out between a fat or oil and an alcohol in the presence of a catalyst comprising a composite metal oxide having a perovskite structure; and a process for preparing an alkyl ester of a fatty acid wherein a transesterification reaction is carried out between a fat or oil and an alcohol in the presence of a catalyst comprising at least one member selected from the group consisting of oxides, hydroxides and carbonates of alkaline earth metals is used as the catalyst, with the alcohol made into a supercritical state or subcritical state. According to the present invention, the alkyl ester of a fatty acid which can be effectively utilized as a diesel fuel oil or the like can be prepared at high efficiency and on an industrial scale mainly from triglyceride contained in a fat or oil, especially a waste oil.

9 Claims, No Drawings

PROCESSES FOR PRODUCING ALKYL ESTER OF FATTY ACID

This application is the national phase under 35 U.S.C. § 371 of PCT International Application No. PCT/JP02/03039 which has an International filing date of Mar. 28, 2002, which designated the United States of America.

TECHNICAL FIELD

The present invention relates to a process for preparing an alkyl ester of a fatty acid.

BACKGROUND ART

Currently, in our country Japan, various edible oils have been used in large amounts. A part of used oil (waste edible oil) is reused as a raw material for soap or the like. However, a majority of the used oil are not collected, and are actually transported to refuse disposal, and incinerated together with burnable refuse, or reclaimed together with unburnable refuse.

On the other hand, there has been previously known that an alkyl ester of a fatty acid can be prepared by subjecting a monoglyceride, a diglyceride or a triglyceride, which is a main component in a vegetable oil, to transesterification reaction with an alkyl alcohol, thereby giving an alkyl ester of a fatty acid (for instance, "*Yuki Kagaku Handobukku* (*Organic Chemistry Handbook*)," published by Gihodo, 1988, p. 1407–1409). Also, by utilizing this reaction, various studies have been made on the techniques for preparing an alkyl ester that can be used as a diesel fuel oil from a vegetable fat or oil, a waste edible oil or the like (for instance, Japanese Patent Laid-Open Nos. Hei 7-197047, Hei 7-310090 and the like). In these techniques, alkyl esters which can meet the requirement of the current Quality Assurance Regulation regarding a gas oil have not been obtained.

Incidentally, since the transesterification reaction is an equilibrium reaction, the equilibrium is shifted to the product side by using an alkyl alcohol, one of the raw materials, in a large amount, or removing glycerol produced as a side reaction product, thereby increasing an yield. Also, this reaction is said to be more advantageous in a vapor phase reaction than in a liquid phase reaction from the viewpoint of state of equilibrium. Further, in order to increase the reaction rate, a catalyst is generally utilized.

In the preparation of acetic acid, a higher fatty acid, an unsaturated carboxylic acid or the like, which is a representative industrial process of the transesterification reaction, an acidic catalyst is generally used in a large amount. For instance, a protonic acid such as sulfuric acid or phosphoric acid has been used as an esterification catalyst for non-aromatic carboxylic acids, and boric acid or sulfuric acid has been used for an esterification of a phenolic acid. However, since these reactions are basically a homogeneous reaction system in which a catalyst exists in the dissolved state in a reaction solution, there has been a problem that the separation and collection of the catalyst from the formed liquid are difficult.

A solid acidic catalyst is also well used. In the transesterification reaction of terephthalic acid or methacrylic acid, there has been used $SO_4^{2-}$—$TiO_2$, $TiO_2$—$SiO_2$, $Al_2(SO_4)_3$/$SiO_2.Al_2O_3$, a sulfonic acid-based ion-exchange resin and the like. In addition, a heteropoly-acid is said to be an excellent esterification catalyst. In a case where the heteropoly-acid is supported to $SiO_2$ or activated charcoal, the heteropoly-acid as a vapor phase catalyst has been known to exhibit an activity which is higher than those of $SiO_2$—$Al_2O_3$ and the solid phosphoric acid. Further, a clay mineral has been also used as a catalyst. Since these solid acidic catalysts and mineral catalysts do not have to be separated from the formed liquid, use of these catalysts is more excellent from the viewpoint of simplification of the reactor. However, these industrial catalysts have a fatal defect that the activity for the transesterification reaction of a fat or oil is low. Therefore, the above process has not yet been actually used on an industrial scale to date.

As a technique for applying a solid acidic catalyst to transesterification of a fat or oil, there has been proposed a technique as disclosed in, for instance, Japanese Patent Laid-Open No. Hei 6-313188. Moreover, the catalyst used in this technique includes a simple or composite metal oxide, a metal sulfate, a metal phosphate, an immobilized acid in which the acid is supported or immobilized to a carrier, a natural mineral and a layered compound, a solid heteropoly-acid, a superacid, a synthetic zeolite, an ion-exchange resin and the like. However, in this technique, the catalytic activity for the transesterification reaction of a fat or oil is as low as that of the conventional processes described above. Therefore, in order to achieve a high yield, there has been necessitated that a ratio of the solid acidic catalyst is increased in the reaction system or that the reaction time is lengthened.

A basic catalyst has been also used in the transesterification reaction, and there has been known that a metal alcoholate is effective as this basic catalyst. Therefore, sodium alcoholate or potassium alcoholate has been generally used as the metal alcoholate. Also, as the basic catalyst, sodium hydroxide, potassium hydroxide, sodium carbonate or the like has been used. These exhibit high activity for the transesterification reaction of a fat or oil. However, the conventional basic catalyst acts in a dissolved state in a reaction solution in the same manner as the acidic catalyst mentioned above. Therefore, the basic catalyst dissolves in the formed liquid, so that the problem that its separation and collection are difficult has not been eliminated.

In addition, there has been attempted to use a solid basic catalyst in the transesterification reaction, and as such a solid basic catalyst, there has been proposed an ion-exchange resin having an amine-based base (for instance, Japanese Patent Laid-Open No. Sho 62-218495). In this technique, the problem of separating and collecting the catalyst is not basically generated. However, this technique is carried out in a reaction system in which the alcohol is used in excess and the concentration calculated as triglyceride, is 0.1 to 3% by weight or so, so that the activity is drastically low, the reaction temperature is also limited to 60° C. or lower from the viewpoint of the durability of the ion-exchange resin, and the like. Therefore, it cannot be said to be practical.

Also, recently, use of a basic solid catalyst comprising a carboxylic acid compound and iron oxide, or a potassium compound and zirconium oxide has been disclosed (Japanese Patent Laid-Open No. 2000-44984). However, its catalytic activity cannot be said to be satisfactory, thereby making it impractical.

In addition, in a case where the basic catalyst is used, other problems are generated besides the problems as mentioned above. In other words, since a natural fat or oil generally contains a large amount of free fatty acids (3% by weight or more on average), if the basic catalyst is used, the side reaction of the formation of the fatty acid soap is drastic, so that there arise some problems that the catalyst is required in excess, that the separation of the fatty acid ester layer and the glycerol layer becomes difficult due to the generated fatty acid soap and the like. Therefore, a pretreatment step of removing a free fatty acid would be necessitated.

From the viewpoint of avoiding the above problems, there has been disclosed, for instance, in Japanese Patent Laid-Open No. Sho 61-14044, a process for converting a free fatty acid to an ester with an acid catalyst as a pretreatment step. However, there arise some problems that the separation of the acid catalyst is difficult, and if the acid catalyst remains in the reaction mixture when the transesterification reaction is carried out, the basic catalyst (a metallic alkali catalyst) is undesirably neutralized, and thereby the amount of the solid catalyst used is increased by the amount of the neutralized catalyst.

In addition, as a process for preparing an ester of a fatty acid not necessitating the pretreatment step as mentioned above, there has been proposed a process of using a solid acidic catalyst (for instance, Japanese Patent Laid-Open No. Hei 6-313188). However, the acidic catalyst has a fatal defect that the activity for the transesterification reaction of a fat or oil is low as compared to that of the basic catalyst, so that there arise a problem that the catalyst is required to be used in a large amount in the transesterification reaction in which the acidic catalyst is used.

Furthermore, there has been known a technique of carrying out the transesterification reaction under high-temperature and high-pressure conditions (240° C., 9 MPa) in the presence of a basic catalyst, thereby increasing the reaction efficiency without requiring the pretreatment. Such a technique is described, for instance, in "JAOCS" (Vol. 61, No. 2, p. 343, 1984). However, since a homogeneously-used catalyst is used, there has been necessitated a purification step as an after-treatment such as removal of the catalyst or removal of the fatty acid soap partially produced.

Moreover, as a process for preparing an alkyl ester of a fatty acid, there has been disclosed a process of carrying out transesterification without a catalyst in an atmosphere in which an alcohol is made into a supercritical state (Japanese Patent Laid-Open Nos. 2000-109883 and 2001-143586). However, its reaction rate is notably smaller as compared to that of the homogeneously-used basic catalyst, and the reaction ratio at an equilibrium reached and the reaction rate are low under the conditions near the supercritical point, thereby making it almost impractical. In order to improve the reaction rate, the conditions of high-temperature and high-pressure must be made stricter. However, there are some problems that the decomposition of the reaction product takes place and that the reaction ratio is consequently lowered, and the like.

DISCLOSURE OF INVENTION

An object of the present invention is to provide a process for preparing an alkyl ester of a fatty acid which can be utilized on an industrial scale, capable of preparing an alkyl ester of a fatty acid effectively utilized as a diesel fuel oil or the like mainly from a triglyceride contained in a fat or oil, especially waste edible oil at a high reaction ratio under practical, relatively mild conditions. In this process, there can be simplified or omitted a step of separating and collecting the catalyst, or in addition to the step, a pretreatment step of removing a free fatty acid contained in the fat or oil, and an after-treatment step of removing a fatty acid soap.

Specifically, the gist of the present invention relates to:
[1] a process for preparing an alkyl ester of a fatty acid characterized by a use of a catalyst comprising a composite metal oxide having a perovskite structure in the preparation of the alkyl ester of a fatty acid by a transesterification reaction between a fat or oil and an alcohol in the presence of the catalyst; and

[2] a process for preparing an alkyl ester of a fatty acid characterized in that in the preparation of the alkyl ester of a fatty acid by a transesterification reaction between a fat or oil and an alcohol in the presence of a catalyst, the alcohol is made into a supercritical state or subcritical state, and at least one member selected from the group consisting of oxides, hydroxides and carbonates of alkaline earth metals is used as the catalyst.

BEST MODE FOR CARRYING OUT THE INVENTION

A first invention of the present invention is directed to a process for preparing an alkyl ester of a fatty acid, wherein a transesterification reaction is carried out between a fat or oil and an alcohol in the presence of a catalyst comprising a composite metal oxide having a perovskite structure; a second invention of the present invention is directed to a process for preparing an alkyl ester of a fatty acid, wherein a transesterification reaction is carried out between a fat or oil and an alcohol in the presence of a catalyst comprising at least one member selected from the group consisting of oxides, hydroxides and carbonates of alkaline earth metals, with the alcohol made into a supercritical state or subcritical state.

One of the significant features of the first invention of the present invention resides in the use of a catalyst comprising a composite metal oxide having a perovskite structure. Since the catalyst is used, the transesterification reaction between an ester (mainly a triglyceride) contained in a fat or oil and an alcohol can be carried out at a high efficiency even under milder conditions, thereby making it possible to prepare on an industrial scale a lower alkyl ester meeting the requirements of the Quality Assurance Regulation regarding a gas oil, which can be effectively utilized as a diesel fuel oil or the like, which had been conventionally difficult. Also, the catalyst is a solid and does not dissolve, for instance, in a reaction solution in which the transesterification reaction is carried out. Since the catalyst can be easily separated and removed from the reaction system with a simple procedure such as filtration after the termination of the reaction, the step of separating and collecting the catalyst can be simplified or omitted. Therefore, an alkyl ester of a fatty acid can be easily purified, and there would be little problem that the catalyst remains in a phase-separated glycerol, so that the resulting glycerol can be immediately reused.

Here, the phrase "lower alkyl ester meeting the requirements of the Quality Assurance Regulation regarding a gas oil" concretely refers to a lower alkyl ester having a sulfur content of 0.2% or less, a cetane number of 45 or more, and a temperature of 90% distillation of 360° C. or lower.

The fat or oil used as a raw material in the present invention is not particularly limited. The fat or oil, for instance, includes natural vegetable fats and oils and animal fats and oils, such as rapeseed oil, sesame oil, soybean oil, corn oil, sunflower oil, palm oil, palm kernel oil, coconut oil, safflower oil, linseed oil, cotton seed oil, tung oil, castor oil, tallow beef fat and pork fat, fish oil; waste edible oils disposed from restaurants, food factories and general households; and the like. Also, these fats and oils can be used alone or in admixture of two or more kinds, and a fat- or oil-processed product comprising the above fat or oil as a main component can also be used as a raw material. In the present invention, it is preferable to use a waste edible oil from the viewpoint of achieving the reuse of the resources.

The quality of the fat or oil used is not particularly limited. It is preferable to use a fat or oil having low contents of water and a solid ingredient, from the viewpoint of achieving the transesterification reaction at a high efficiency. Therefore, when the waste edible oil is used as a raw material, it is preferable that the waste edible oil is pretreated in order to remove water and a solid ingredient contained therein. Also, there may be some cases where an acidic substance is contained in a large amount in a waste edible oil used. It is preferable that the waste edible oil is subjected to deacidification as a pretreatment from the viewpoint of preventing the inhibition of the catalytic activity by the acidic substance. Here, any of the above pretreatments can be carried out by a known method.

The alcohol used in the present invention is not particularly limited. A lower alcohol having a saturated, linear or branched hydrocarbon backbone preferably having 1 to 8 carbon atoms, more preferably having 1 to 5 carbon atoms is preferable, from the viewpoint of preparing a high-quality lower alkyl ester used as a diesel fuel oil. The alcohol includes, for instance, methyl alcohol, ethyl alcohol, propyl alcohol, isopropyl alcohol, butyl alcohol, t-butyl alcohol and the like. Among them, at least one member selected from the group consisting of methyl alcohol, ethyl alcohol, propyl alcohol and isopropyl alcohol is more preferable, and methyl alcohol is still more preferable, from the viewpoints of low cost and facilitation in collection.

The catalyst used in the present invention is a catalyst comprising a composite metal oxide having a perovskite structure, wherein the composite metal oxide has a composition represented by the general formula: $ABO_n$, wherein A is an alkaline earth metal atom, B is a transition metal atom, and n is an integer of 3 or more. From the viewpoint of exhibiting the desired effects of the present invention, A is preferably at least one member selected from the group consisting of Ca, Sr and Ba, and B is preferably at least one member selected from the group consisting of Ti, Mn, V, Fe, Cu, Y and La, which is a lanthanide metal atom. Further, as the above catalyst, more preferable are those comprising a composite metal oxide in which A is at least one member selected from the group consisting of Ca, Sr and Ba, and B is at least one member selected from the group consisting of Ti, Mn, Y and La. Here, the perovskite structure is a structure generally formed in a case where A ion is notably large in the structure having a composition of $ABO_3$. An oxide includes $A_{+1}B_{+5}O_3$, $A_{+2}B_{+4}O_3$, $A_{+3}B_{+3}O_3$, and the like. Thus, the perovskite structure refers to a structure of a composite perovskite compound containing plural A or B ions, the structure of which is determined by X-ray diffraction.

In addition, as the above catalyst, those further comprising a cesium (Cs) compound are preferable. The Cs compound includes, for instance, $Cs_2O$, $CsCl$, $CsF$, $Cs_2CO_3$, $CsNO_3$, $Cs_2SO_4$, and the like. The content of the compound is not particularly limited as long as the desired effects of the present invention are obtained, and is preferably from 1 to 10% by mass, more preferably from 3 to 8% by mass, as calculated by the mass of cesium. Among them, as the catalyst comprising the Cs compound, those comprising a composite metal oxide in which A is at least one member selected from the group consisting of Ca, Sr and Ba, and B is at least one member selected from the group consisting of Ti, Mn, Y and La, together with the Cs compound are preferable.

It is considered that the catalyst comprising the composite metal oxide having a perovskite structure used in the present invention is a solid, strongly basic catalyst, in which the composite metal oxide is deduced to form a stable structure comprising oxides of a basic metal atom having a relatively larger radius such as alkaline earth metal atoms and lanthanide metal atoms; and since the composite metal oxide especially has a perovskite structure, the basic metal oxide having a large ionic radius is structurally stabilized, so that structural change of the catalyst is less likely to be caused when the catalyst is used in the reaction as a catalyst. In addition, although the compound itself having a perovskite structure has a strong basicity, it is deduced that even if a Cs-containing compound having a large ionic radius is further added to the catalyst, the perovskite structure is stably maintained, thereby establishing additive property of basicity of both compounds, so that the basicity of the catalyst is increased more by further addition of the Cs compound to the catalyst. Therefore, the catalyst forms a material system having remarkably large basic strength as the basicity which can be expected for the composite metal oxide, so that the catalyst can be a catalyst having a more excellent activity. Therefore, according to the catalyst of the present invention, a high catalytic activity is exhibited in the transesterification reaction, so that a desired lower alkyl ester which can be effectively utilized as a diesel fuel oil or the like can be obtained at a high efficiency, which had been conventionally difficult. In addition, since the catalyst is a solid, the separation and collection of the catalyst after the termination of the reaction are facilitated, and there is no limitation on the reaction temperature under ordinary esterification reaction conditions, which is different from that of the above known solid basic catalyst made of an ion exchange resin having an amine-based base.

The preparation of the catalyst of the present invention is carried out by mixing and supporting each metal used as a raw material to each other by coprecipitation method, impregnation method, kneading method or the like, and baking the resulting mixture. Specifically, the preparation can be carried out, for instance, by mixing aqueous solutions containing each metal used as a raw material with stirring, aging the mixture, thereafter obtaining a precipitate, washing, filtering, drying and baking the precipitate. Further, the catalyst obtained as a powder can be molded to give a so-called "solid catalyst," which is preferable because the possibility of admixing the catalyst into a reaction solution can be dramatically reduced, and the step of separation and collection of the catalyst after the termination of the reaction does not substantially have to be carried out.

In the preparation of the aqueous solution containing each metal used as a raw material, there can be used a carbonate, a nitrate, a sulfate, a formate, an acetate or the like, each containing A shown in the above general formula; and a carbonate, a nitrate, a sulfate, a formate, an acetate or the like, each containing B shown in the above general formula. The concentration of the metal in the aqueous solution is not particularly limited as long as the aqueous solution of the metal is obtained. Next, the aqueous solution containing each metal is mixed at preferably from 30° to 60° C. with stirring. The mixing is carried out in the presence of an alkali metal, which acts as an agent for increasing pH of the aqueous solution as a precipitating agent, and is not contained in the catalyst, from the viewpoint of forming a precipitate of a hydroxide having a uniform composition from each metal salt. For instance, an aqueous solution of Na salt may be prepared, and mixed with an aqueous solution containing each of the above metals used as a raw material. The mixing may be carried out by, for instance, supplying each of the resulting aqueous solutions at once in one vessel.

It is preferable that an aqueous solution containing each metal used as a raw material is added dropwise against an aqueous solution containing an alkali metal, from the viewpoint of efficiently progressing the formation of the catalyst. It is desired in the mixing that the metal of the component A and the metal of the component B are added at a molar ratio of preferably 1:1. Also, it is desired that the alkali metal is used so that a molar ratio between the alkali metal and a total of the metals of the components A and B is preferably from 1:1 to 5:1. The method of stirring is not particularly limited.

The aging refers to a step of growing the core formed during the precipitation, which is preferably carried out at the same temperature range as that in mixing and stirring of the above aqueous solution for 1 to 4 hours. By this step, since the solid particles of the formed catalyst can be obtained as a precipitate, the precipitate is washed by washing with water and filtration. After washing, the precipitate is properly dried by, preferably air-drying at 30° to 80° C., and further baked in a muffle furnace at preferably 500° C. or higher, more preferably from 800° to 1000° C. for 1 to 4 hours.

In a case where the Cs compound is to be contained in the catalyst, it can be carried out properly mixing a powder of a catalyst obtained after drying with a powder of a Cs compound, for instance, $Cs_2O_3$, $Cs_2CO_3$, $CsNO_3$, $Cs_2SO_4$, $CsCl$, $CsCOOCH_3$, $Cs_2O$, and the like, and thereafter baking the mixture in the same manner as mentioned above.

The catalyst can be molded by a known method. The term "molding" as used herein also includes an embodiment where a powdery catalyst is supported onto a specified carrier in addition to an embodiment where a powdery catalyst is molded into a given shape with a pressing machine or the like.

The shape of the solid catalyst obtained by molding the catalyst of the present invention is not particularly limited, and any one can be appropriately selected in accordance with the application. The shape may be any of, for instance, tablet form, ring form, pelletal form, honeycomb form and corrugated form, or those prepared by wash-coating a slurry containing a powdery catalyst onto a carrier made of ceramic, a metallic honeycomb or the like.

The process for preparing an alkyl ester of a fatty acid of the present invention may be a continuous process in which the transesterification reaction is carried out by continuously feeding the raw materials, or a batch process in which the transesterification reaction is carried out once by feeding the raw materials in an amount required for one batch. In a case of the continuous process, for instance, there can be carried out the process by continuously feeding a fat or oil and an alcohol, which are raw materials, to a reactor for carrying out the transesterification reaction, and discharging an alkyl ester of a fatty acid and glycerol, which are reaction products, and a residual fat or oil and alcohol, which are unreacted substances, wherein a fixed bed, flow-type reactor in which a solid catalyst prepared by molding the catalyst (powder) of the present invention is filled and fixed is used as the reactor. On the other hand, in a case of the batch process, there can be carried out the process by introducing each of a fat or oil, an alcohol and a catalyst, which are raw materials to a reactor used for carrying out the transesterification reaction in an amount required for one batch to carry out the reaction, and taking out the reaction mixture comprising an alkyl ester of a fatty acid and glycerol, which are reaction products, and a residual fat or oil and alcohol, which are unreacted substances. Among them, the embodiment of carrying out the preparation of the alkyl ester of a fatty acid by carrying out the transesterification reaction using a fixed bed, flow-type reactor, in which a solid catalyst prepared by molding the catalyst (powder) of the present invention is filled and fixed is preferable because the reaction can be progressed in a high efficiency, and the step of separating and collecting the catalyst can be also omitted after the termination of the reaction. In a case of the batch process, the catalyst can be also easily removed by filtration or the like, so that the step of separating and collecting the catalyst can be simplified.

The present invention will be explained hereinbelow for a case of preparing a lower alkyl ester using the above fixed bed, flow type reactor, which is a preferred embodiment as the process for preparing an alkyl ester of a fatty acid of the present invention. Here, in the following explanations, "parts" represents "parts by weight" unless specified otherwise.

The amount of the lower alcohol charged to the fat or oil is preferably from 10 to 100 parts, preferably from 10 to 40 parts, based on 100 parts of the fat or oil. However, the amount of the lower alcohol charged to 100 parts of the fat or oil, which is the raw material, is changeable depending on an average molecular weight of the fat or oil. In the case, the amount charged can be approximately expressed as a multiple of chemical equivalent which is calculated by the following equation (1). In other words, if the average molecular weight of the fat or oil is represented by Mo and the average molecular weight of the fat or oil is represented by Ma, the equivalent (Wa) charged of the lower alcohol is calculated by the following equation:

$$Wa=100/Mo\times 3Ma \tag{1}$$

The lower alcohol is charged at a ratio of preferably from 1.2- to 10-folds, more preferably from 1.5- to 5-folds equivalent Wa charged. If the charging ratio of the alcohol is within the above range, the transesterification reaction is sufficiently progressed, thereby making it also preferable from the economic viewpoint. Here, the average molecular weight is each calculated on the basis of the composition of the fat or oil and the lower alcohol used as raw materials.

For instance, when the average molecular weight of the fat or oil is 880 and the lower alcohol is methyl alcohol (average molecular weight: 32), methyl alcohol is charged in an amount of preferably from 12 to 100 parts, more preferably from 15 to 50 parts, based on 100 parts of the fat or oil.

The amount of the solid catalyst charged to the reactor is not particularly limited as long as the desired efficiency for the transesterification reaction is obtained. Generally, the amount of the solid catalyst charged is preferably from 0.5 to 100 parts, more preferably from 1 to 30 parts, based on 100 parts of the fat or oil. As long as the amount of the solid catalyst charged is within the above range, the transesterification reaction is sufficiently progressed, thereby making it also preferable from the economic viewpoint.

The reactor, namely the vessel for providing a reaction site for the transesterification reaction, includes flasks, steel vessels, steel pipes, static mixers, agitation vessels and the like. The materials of the reactor are not particularly limited, and there can be used glass, steel, stainless steel, Ni alloys, Ti alloys, glass lining steel, polymer lining steel, ceramic lining steel and the like.

The fat or oil and the lower alcohol may be fed to the reactor, for instance, by separately feeding via raw material feeding lines connected between raw material tanks and the reactor (embodiment 1); or previously mixing a fat or oil and a lower alcohol in one raw material tank, and feeding both the components simultaneously via one raw material feeding line (embodiment 2). The order of the charging of each raw material is not particularly limited. In addition, the embodiment 2 is intended to encompasses all the embodiments in which both components are mixed and simultaneously fed to the reactor. For instance, there may be included an embodiment where the raw material tank is provided for each raw material and the raw material feeding lines are united into one line, so that a so-called line-mixing is carried out and both components are simultaneously fed to the reactor.

In the case of the embodiment 1, the feed amount of the fat or oil to the solid catalyst in the reactor is preferably from 0.1 to 10/hr in terms of the liquid space velocity (LHSV). In addition, the feed amount of the lower alcohol is preferably such that the amount of the lower alcohol charged to the fat or oil is the above preferred range, preferably from 0.01 to 6/hr in terms of the liquid space velocity (LHSV).

In the case of the embodiment 2, the fat or oil and the lower alcohol are previously mixed so that the amount of the lower alcohol charged to the fat or oil is within the above preferred range, and the resulting mixture is fed to the solid catalyst in the reactor preferably at 0.7 to 8/hr in terms of the liquid space velocity (LHSV).

The liquid space velocity as used herein is a value obtained under the conditions of 25° C. and 1 atmosphere.

The transesterification reaction is carried out by heating each of the fed raw materials to a given reaction temperature in the reactor. Here, the method of heating may be charging each raw material with heating the raw material by using a heat exchanger during charging, or heating the reactor externally from the beginning of charging. The reaction temperature is preferably from 25° to 300° C., more preferably from 40° to 200° C., still more preferably from 55° to 60° C. In the present invention, it is especially preferable to carry out the reaction at a temperature range of from 55° to 60° C. This is due to the fact that the above temperature range is a very mild condition, and especially has excellent contribution to cost reductions of the equipments and facilitation of the operation.

The reaction pressure corresponds to a vapor pressure at the reaction temperature exhibited by a volatile substance charged in the reactor. The reaction pressure is preferably from 0.1 to 10 MPa, more preferably from 0.1 to 6 MPa, still more preferably from 0.1 to 1 MPa. As long as the reaction temperature and the reaction pressure are within the above ranges, it is preferable because the rate for the transesterification reaction is sufficient, so that the reaction can be excellently and rapidly progressed. The reaction time cannot be absolutely determined because the reaction time differs depending upon the reaction temperature and the kind of the raw materials used. The reaction time is generally selected within the range of from 1 minute to 24 hours.

The reaction product obtained by the transesterification reaction in the reactor is a mixture comprising as main components glycerol and a lower alkyl ester of a fatty acid formed by the transesterification reaction of a lower alcohol and a triglyceride contained as a main component in the fat or oil used as a raw material. In order to separate the lower alkyl ester and glycerol from this mixture, there can be applied a stand-still phase separation (decantation) method comprising cooling the resulting reaction mixture to a given temperature after the termination of the reaction, allowing the mixture to stand at the above temperature or at room temperature, or after the termination of the reaction, directly allowing the mixture to stand at room temperature, to cause phase separation between the lower alkyl ester and the glycerol utilizing their difference in specific gravity. However, the centrifugation method described below is preferable from the viewpoint of productivity.

The centrifugation method is carried out by subjecting the reaction mixture cooled to a desired temperature after the termination of the reaction to a centrifugal separator, and applying a centrifugal force to a degree that the lower alkyl ester and the glycerol can be separated. In the upper layer obtained after the centrifugation, there are contained admixtures of an unreacted alcohol component, an odorous component, a colored component and the like besides the main component lower alkyl ester. Therefore, if the admixtures are subsequently removed by a known purification step using, for instance, distillation or adsorbent agent, a lower alkyl ester can be obtained in a high purity. Here, the adsorbent agent which can be used in the purification step includes, for instance, activated charcoal, active carbon fiber, activated clay, acidic clay, bentonite, diatomaceous earth, activated alumina and the like.

One of the significant features of the second invention resides in that a transesterification reaction between an ester (mainly a triglyceride) contained in a fat or oil and an alcohol is carried out in the co-presence of at least one member selected from the group consisting of oxides, hydroxides and carbonates of alkaline earth metals as a catalyst, with the alcohol made into a supercritical state or subcritical state. According to the present invention, the transesterification reaction can be carried out at a high efficiency between the ester contained in a fat or oil and the alcohol under practical, mild conditions as compared to the above supercritical reaction system of an alcohol in the absence of a catalyst, so that there can be prepared on an industrial scale a lower alkyl ester meeting the requirement of the Quality Assurance Regulation concerning a gas oil, which can be effectively utilized as a diesel fuel oil, which had been conventionally difficult. In this invention, the reaction is carried out in the presence of the above catalyst, with the alcohol made into a supercritical state or subcritical state; in other words, the alcohol maintained under high-temperature and high pressure conditions to activate the alcohol. Therefore, as compared to the neutralization reaction of a free fatty acid contained in the fat or oil with an alkaline earth metal contained in the catalyst, the progress of the esterification reaction of the fatty acid with the alcohol would be prioritized. Therefore, a pretreatment step of esterifying or removing the fatty acid and an after-treatment step of removing a fatty acid soap would not be necessitated. Also, the catalyst is a solid and does not dissolve in, for instance, a reaction solution in which the transesterification reaction is carried out. Therefore, the catalyst can be easily separated and removed from the reaction system with a simple procedure such as filtration after the termination of the reaction, so that the step of separating and collecting the catalyst can be simplified or omitted. Therefore, an alkyl ester of a fatty acid can be easily purified and there would be little problem that the catalyst remains in a phase-separated glycerol. The resulting glycerol can be immediately reused.

The fat or oil used as a raw material in this invention is not particularly limited. The fat or oil, for instance, includes those exemplified above. Like in the above first invention, it is preferable to use waste edible oil from the viewpoint of achieving reuse of the resources. In addition, the quality of the fat or oil used may be the same as that of the above first invention. The above pretreatment may be carried out for removal of water or the like and deacidification as desired.

Also, the alcohol used in this invention may be the same as those of the above first invention.

In this invention, there is used as a catalyst at least one member selected from the group consisting of oxides, hydroxides and carbonates of alkaline earth metals. The alkaline earth metal is preferably at least one member selected from the group consisting of Mg, Ca, Sr and Ba, more preferably Mg. Preferred examples of the catalyst include MgO, Mg(OH)$_2$, MgCO$_3$, CaO, Ca(OH)$_2$, CaCO$_3$, and the like.

Since the catalyst is a solid, the separation and collection of the catalyst after the termination of the reaction are facilitated. In addition, the catalyst can be molded to give a so-called "solid catalyst," which is preferable because the possibility of admixing the catalyst into the reaction solution can be dramatically reduced, and the step of separation and collection of the catalyst after the termination of the reaction does not substantially have to be carried out. The shape of the solid catalyst includes, for instance, those exemplified above.

In the preparation of an alkyl ester of a fatty acid of the present invention, the transesterification reaction is carried out in the co-presence of at least one member selected from the group consisting of oxides, hydroxides and carbonates of alkaline earth metals as a catalyst, with the alcohol made into a supercritical state or subcritical state. So far, as mentioned above, there has been known the process for preparing of a fatty acid ester by carrying out a transesterification reaction in the absence of a catalyst with an alcohol made into a supercritical state. However, this process could not be satisfactory for practical uses from the viewpoints of reaction efficiency and reaction rate. On the other hand, the present invention has a constitution that the alcohol is activated by making the alcohol into a supercritical state or subcritical state, and the activation of the alcohol and the specified catalyst are combined. In a case where an alkali metal catalyst which has been conventionally used as a catalyst for transesterification reaction is used as the catalyst, since the alkali metal catalyst is strongly basic, a neutralization reaction with an acidic component, especially a free fatty acid, contained in the raw material fat or oil, irreversibly takes place, so that a fatty acid soap is generated in a large amount, thereby causing worsening influences to the step subsequent to the transesterification reaction. In other words, an ester-containing phase and a glycerol phase are emulsified, thereby making it difficult to separate the phases. Also, the catalyst itself has to be used in a large amount. Therefore, in such a case, the desired effects of the present invention cannot be obtained. In the present invention, there are surprisingly exhibited excellent desired effects of the present invention which cannot be anticipated from those of the prior arts by using as the "specified catalyst" an oxide of an alkaline earth metal or the like, which has not been ordinarily used as a catalyst for transesterification reaction because of low efficiency of the reaction. In a case where the transesterification reaction is carried out by combining the activation of the alcohol and the catalyst comprising an oxide of an alkaline earth metal or the like, it is deduced that the basicity of the catalyst is weak, so that under the conditions that the alcohol is made into a supercritical state or subcritical state, the free fatty acid is esterified before the neutralization reaction takes place with an acidic substance, especially a free fatty acid, and so that further the neutralization reaction, if caused at all, is reversible, whereby the free fatty acid involved in the neutralization reaction can be also esterified.

For instance, in a case where methyl alcohol is used as an alcohol, the methyl alcohol in a supercritical state or subcritical state is activated by dissociating as follows:

It is deduced that the proton (H$^+$) generated by the dissociation of methyl alcohol activates the ester (mainly a triglyceride) contained in the fat or oil together with the catalyst, an oxide of an alkaline earth metal or the like, thereby effectively progressing the transesterification reaction between the methyl alcohol and the ester. On the other hand, it is deduced that since the free fatty acid contained in the fat or oil is immediately esterified by activated methyl alcohol, the neutralization reaction with the alkaline earth metal contained in the catalyst is hardly likely to take place, and that even if the neutralization reaction takes place, the product is dissociated again and the resulting free fatty acid is esterified.

The process for preparing an alkyl ester of a fatty acid of the present invention may be a batch process in which the transesterification reaction is carried out once by feeding the raw materials in an amount required for one batch, or a continuous process in which the transesterification reaction is carried out by continuously feeding the raw materials. In a case of the batch process, there can be carried out the process by introducing each of a fat or oil, an alcohol and a catalyst, which are raw materials to a reactor used for carrying out the transesterification reaction, in an amount required for one batch to carry out the reaction, and taking out the reaction mixture comprising an alkyl ester of a fatty acid and glycerol, which are reaction products, and a residual fat or oil and alcohol, which are unreacted substances. On the other hand, in a case of the continuous process, there can be carried out the process by continuously feeding a fat or oil and an alcohol, which are raw materials, to a reactor for carrying out the transesterification reaction, and discharging an alkyl ester of a fatty acid and glycerol, which are reaction products, and a residual fat or oil and alcohol, which are unreacted substances, wherein a fixed bed, flow-type reactor in which a solid catalyst prepared by molding the catalyst of the present invention is filled and fixed is used as the reactor. Among them, the embodiment of carrying out the preparation of the alkyl ester of a fatty acid by carrying out the transesterification reaction using a fixed bed, flow-type reactor, in which a solid catalyst prepared by molding the catalyst of the present invention is filled and fixed is preferable from the viewpoint that the control of the reaction time under high-temperature and high-pressure conditions is further facilitated in the process for preparing an alkyl ester of a fatty acid of this invention in which the transesterification reaction is carried out with the alcohol maintained in a supercritical state or subcritical state. In addition, it is preferable because the reaction can be progressed in a high efficiency, and the step of separating and collecting the catalyst after the termination of the reaction can be also omitted. In the case of the batch process, the catalyst can also be easily removed by filtration or the like, so that the step of separating and collecting the catalyst can be simplified.

The present invention will be explained hereinbelow for a case where the above fixed bed, flow type reactor is used, which is a preferred embodiment as the process for preparing an alkyl ester of a fatty acid of the present invention. Here, in the following explanations, "parts" represents "parts by weight" unless specified otherwise.

The amount of the alcohol charged to the fat or oil is preferably from about 1.2- to about 50-folds, more preferably from about 1.2- to about 30-folds stoichiometrically required amount to triglyceride contained in the fat or oil as calculated on a molar basis. The amount is about 1.2-folds or more from the viewpoint of excellently maintaining a supercritical state or subcritical state of the alcohol up to the termination of the reaction, and the amount is about 50-folds or less from the viewpoint of maintaining high volume efficiency of the reaction vessel and high reaction efficiency. Here, the stoichiometrically required amount of the alcohol to the fat or oil is each calculated on the basis of the component composition of the fat or oil and the lower alcohol used as the raw material.

The amount of the solid catalyst charged to the reactor is not particularly limited as long as the desired efficiency for the transesterification reaction is obtained. Generally, the amount of the solid catalyst charged is preferably from 0.5 to 100 parts, more preferably from 1 to 30 parts, based on 100 parts of the fat or oil. As long as the amount of the solid catalyst charged is within the above range, the transesterification reaction is sufficiently progressed, thereby making it also preferable from the economic viewpoint.

The reactor for carrying out the transesterification reaction and its material include, for instance, those exemplified above.

The embodiment for feeding the fat or oil and the alcohol to the reactor includes, for instance, the above embodiment 1 and embodiment 2.

In this invention, in both cases of the embodiment 1 and the embodiment 2, the feed amount of the fat or oil to the solid catalyst in the reactor is preferably from 1 to 30/h, more preferably from 1.5 to 20/h, in terms of the liquid space velocity (LHSV). The feed amount is 1/h or more, from the viewpoint of the productivity per unit capacity of the reactor, and the feed amount is 30/h or less, from the viewpoint of sufficiently carrying out the reaction in a high reaction rate.

On the other hand, the feed amount of the alcohol is preferably such that the amount of the alcohol charged to the fat or oil is the above preferred range, which can be determined depending upon the feed amount of the fat or oil.

The transesterification reaction is carried out in the reactor by controlling the pressure and the temperature so that the fed alcohol is made into a supercritical state or subcritical state. The temperature and the pressure at which the present invention is carried out may differ depending upon the kinds of the alcohol. For instance, in a case where methyl alcohol is used, the reaction temperature is usually preferably from 200° to 300° C., more preferably from 220° to 280° C. The reaction pressure corresponds to a vapor pressure at the reaction temperature shown by a volatile substance charged in the reactor. Usually, the overall pressure inside the reactor is preferably from 3 to 15 MPa, more preferably from 5 to 13 MPa. As long as the reaction temperature and the reaction pressure are within the above ranges, it is preferable because the alcohol is sufficiently activated, the thermal decomposition of the substances involved in the reaction is suppressed, and also it is economically advantageous. Further, the balance between the reaction temperature and the reaction pressure is important in the sufficient activation of the alcohol. From this viewpoint, the combination of preferable reaction temperature and reaction pressure includes the conditions where the reaction temperature is from 220° to 280° C. and the reaction pressure is from 5 to 13 MPa, namely the conditions at which the alcohol is in a subcritical state. In this invention, it is especially preferable that the transesterification reaction is carried out by making the alcohol in a subcritical state from the viewpoint of totally improving the productivity of the alkyl ester of a fatty acid especially in consideration of the cost reduction of the equipments and facilitation of the operation.

The reaction time cannot be absolutely determined because the reaction time differs depending upon the reaction temperature and the kinds of the raw materials used and the like. The reaction time is generally selected from the range of 1 minute to 24 hours. For instance, in a case where the reaction is carried out under temperature conditions exceeding 250° C., the reaction time is preferably within 60 minutes, more preferably within 40 minutes in order to suppress the thermal decomposition of the glycerol or the like generated during the reaction.

Here, the method of heating the raw materials may be charging each raw material with heating the raw material by using a heat exchanger during charging, or heating the reactor externally from the beginning of charging. Also, during the reaction, there may be some cases where a free fatty acid is partly adsorbed to an oxide of an alkaline earth metal, which is the catalyst, in equilibrium, thereby generating the deterioration of the catalytic activity. In such case, the regeneration of the catalyst can be readily carried out by feeding a hot air at a high temperature, preferably about 500° to about 600° C. to the catalyst, to carry out oxidative decomposition of the adsorbed fatty acid.

The reaction product obtained by the transesterification reaction in the reactor is a mixture comprising as main components glycerol and an alkyl ester of a fatty acid formed by the transesterification reaction of an alcohol and a triglyceride contained as a main component in the fat or oil used as raw materials. The separation of the alkyl ester of a fatty acid and glycerol from this mixture can be carried out in the same manner as described above. In addition, the removal of the admixtures of an unreacted alcohol component, an odorous component, a colored component and the like can be carried out in the same manner as described above.

The alkyl ester of a fatty acid obtained by the process for preparing a fatty acid ester of the present invention in the manner described above has a sufficiently high purity, and can be directly used as a gas oil substitute fuel or the like. Also, since glycerol does not contain the catalyst, the glycerol can be immediately reused.

EXAMPLES

The constitution and the function and effects of the present invention will be specifically explained by means of Examples. The present invention is by no means limited by the examples, and any of modes with appropriate modifications within the range which can match the gist described above and below are encompassed within the technical scope of the present invention.

Example 1-1

An aqueous solution prepared by dissolving 46 g of $Na_2CO_3$ in 540 ml of water was kept at 60° C. with stirring, and an aqueous solution prepared by dissolving 22.4 g of $Ca(NO_3)_2 \cdot 4H_2O$ and 28.3 g of $TiOSO_4 \cdot nH_2O$ in 586 ml of water was added dropwise thereto. Thereafter the mixture was aged for 1 hour, to give a precipitate. The precipitate was filtered, washed with water, and filtered, and thereafter the residue was dried, and baked at 800° C. for 2 hours. An X-ray diffraction image of the resulting powder had a perovskite structure. Here, the X-ray diffraction was carried out by RAD-IIB manufactured by Rigaku Denki. The baked product thus obtained was molded into a tablet form with a hydraulic pressing molding machine, and the molded product was cut into 2 to 3 mm pieces, and the pieces were filled and fixed in the reactor as a catalyst. Subsequently, the reaction was started with feeding the raw materials. Here, the transesterification reaction was carried out under the following reaction conditions.

(Reaction Conditions)

Raw material fat or oil: edible rapeseed oil+edible soybean oil (manufactured by THE NISSIN OIL MILLS, LTD.)

Raw material alcohol: methyl alcohol

Amount of catalyst: 10 ml (about 20 parts by weight based on 100 parts by weight of the fat or oil)

Feeding rate of fat or oil (LHSV): 2/h

Feeding rate of alcohol (LHSV): 0.26/h

Amount of alcohol charged: 13 parts by weight based on 100 parts by weight of the fat or oil Reaction temperature: 60° C.

Reaction pressure: normal pressure (0.1 MPa)

After 1 hour passed from the beginning of the reaction, the generated solution was sampled every hour, and methyl alcohol was removed with an evaporator from the methyl ester phase of the sample, and thereafter the viscosity of the methyl ester solution was determined, and the ratio of methyl ester generated was obtained. The ratio of methyl ester generated means the mass ratio (%) occupied with the methyl ester in the methyl ester phase (including triglyceride) of the generated solution from which methyl alcohol was removed. Here, the determination of the viscosity was carried out with a viscosity analyzer [BL-type viscometer (manufactured by TOKIMEC, INC.)]. The amount of methyl ester in the methyl ester phase was obtained by preparing a calibration curve by obtaining viscosities of the methyl ester solutions of known concentrations, and determining the amount from the calibration curve.

The ratio (%) of methyl ester generated obtained by analyzing the sample 3 hours after the beginning of the reaction is shown in Table 1.

Example 1-2

The same procedures as in Example 1-1 were carried out except that 28.6 g of $Na_2CO_3$ was dissolved in 337 ml of water, and that 17.7 g of $Ca(NO_3)_2.4H_2O$ and 21.5 g of $Mn(NO_3)_2.6H_2O$ were dissolved in 273 ml of water, to prepare a catalyst. According to the X-ray diffraction, the catalyst was found to have a perovskite structure. The transesterification reaction was carried out in the same manner as in Example 1-1, and the ratio of methyl ester generated at this time was determined. The results are shown in Table 1.

Comparative Examples 1-1 and -2

The transesterification reaction was carried out in the same manner as in Example 1-1 except that one prepared by baking each of CaO and $TiO_2$ at 800° C. was used as a catalyst, and the ratio of methyl ester generated at this time was determined. As a result of the X-ray diffraction, it was confirmed that the catalyst did not have a perovskite structure. The results are shown in Table 1.

Example 1-3

In 405 ml of water was dissolved 33.3 g of $Na_2CO_3$, and 19.0 g of $Sr(NO_3)_2$ and 16.8 g of $TiOSO_4.nH_2O$ were dissolved in 415 ml of water, and thereafter a precipitate was obtained in the same manner as in Example 1-1. The amount 18.2 g of a dried precipitate and 1.82 g of $Cs_2O_3$ were mixed, and then the resulting mixture was baked at 800° C. for 2 hours, and thereafter the catalyst was prepared in the same manner as in Example 1-1. According to the X-ray diffraction, the catalyst was found to have a perovskite structure. The transesterification reaction was carried out in the same manner as in Example 1-1, and the ratio of methyl ester generated at this time was determined. The results are shown in Table 1.

Example 1-4

The catalyst was prepared in the same manner as in Example 1-3 except that 49.8 g of $Na_2CO_3$ was dissolved in 588 ml of water, and that 28.15 g of $La(NO_3)_3.6H_2O$, 15.4 g of $Ca(NO_3)_2.4H_2O$ and 31.4 g of $Cu(NO_3)_2.3H_2O$ were dissolved in 474 ml of water. According to the X-ray diffraction, the catalyst was found to have a perovskite structure. The transesterification reaction was carried out in the same manner as in Example 1-1, and the ratio of methyl ester generated at this time was determined. The results are shown in Table 1.

Example 1-5

The catalyst was prepared in the same manner as in Example 1-3 except that 25.4 g of $Na_2CO_3$ was dissolved in 300 ml of water, and that 9.6 g of $Y(NO_3)_2.6H_2O$, 13.1 g of $Ba(NO_3)_2$ and 24.2 g of $Co(NO_3)_2.3H_2O$ were dissolved in 318 ml of water. According to the X-ray diffraction, the catalyst was found to have a perovskite structure. The transesterification reaction was carried out in the same manner as in Example 1-1, and the ratio of methyl ester generated at this time was determined. The results are shown in Table 1.

Example 1-6

The catalyst was prepared in the same manner as in Example 1-3 except that 38.2 g of $Na_2CO_3$ was dissolved in 450 ml of water, and that 43.3 g of $La(NO_3)_3.6H_2O$, 21.2 g of $Sr(NO_3)_2$ and 29.1 g of $Co(NO_3)_2.6H_2O$ were dissolved in 545 ml of water. According to the X-ray diffraction, the catalyst was found to have a perovskite structure. The transesterification reaction was carried out in the same manner as in Example 1-1, and the ratio of methyl ester generated at this time was determined. The results are shown in Table 1.

Example 1-7

The catalyst was prepared in the same manner as in Example 1-3 except that 38.2 g of $Na_2CO_3$ was dissolved in 450 ml of water, and that 43.3 g of $La(NO_3)_3.6H_2O$, 21.2 g of $Sr(NO_3)_2$ and 40.4 g of $Fe(NO_3)_3.9H_2O$ were dissolved in 545 ml of water. According to the X-ray diffraction, the catalyst was found to have a perovskite structure. The transesterification reaction was carried out in the same manner as in Example 1-1, and the ratio of methyl ester generated at this time was determined. The results are shown in Table 1.

Comparative Examples 1-3 and -4

The transesterification reaction was carried out in the same manner as in Example 1-1 except that one prepared by baking each of BaO and SrO at 800° C. was used as a catalyst, and the ratio of methyl ester generated at this time was determined. As a result of the X-ray diffraction, it was confirmed that the catalyst did not have a perovskite structure. The results are shown in Table 1.

Comparative Example 1-5

The transesterification reaction was carried out in the same manner as in Example 1-1 except that one prepared by mixing 20 g of $TiO_2$ and 2 g of $Cs_2CO_3$, and baking the mixture at 800° C. was used as a catalyst, and the ratio of methyl ester generated at this time was determined. As a result of the X-ray diffraction, it was confirmed that the catalyst did not have a perovskite structure. The results are shown in Table 1.

TABLE 1

| | Composition of Catalyst | Ratio of Methyl Ester Generated (%) |
|---|---|---|
| Ex. 1-1 | $CaTiO_3$ | 92.1 |
| Ex. 1-2 | $CaMnO_3$ | 88.0 |
| Comp. Ex. 1-1 | CaO | 10.0 |
| Comp. Ex. 1-2 | $TiO_2$ | 0 |
| Ex. 1-3 | $Cs_2O/SrTiO_2$ | 84.0 |
| Ex. 1-4 | $Cs_2O/La_2CaCu_2O_6$ | 92.0 |
| Ex. 1-5 | $Cs_2O/YBa_2Cu_4O_8$ | 84.5 |
| Ex. 1-6 | $Cs_2O/LaSrCoO_4$ | 88.3 |
| Ex. 1-7 | $Cs_2O/LaSrFeO_3$ | 86.0 |
| Comp. Ex. 1-3 | BaO | 0 |
| Comp. Ex. 1-4 | SrO | 1.2 |
| Comp. Ex. 1-5 | $Cs_2O/TiO_2$ | 20.8 |

*: All of the contents of the Cs compound in the catalysts of Examples 1-3 to -7 and Comparative Example 1-5 were about 6% by mass calculated as the mass of Cs.

It can be seen from the comparisons of Examples 1-1 to -7 with Comparative Examples 1-1 to -5 that the ratio of methyl ester generated is remarkably improved by preparing a methyl ester using the catalyst comprising a composite metal oxide and having a perovskite structure, as compared to a case where the catalyst is not used.

Example 2-1

An edible rapeseed oil and an edible soybean oil (both manufactured by THE NISSIN OIL MILLS, LTD.) at a rate of 0.09 g per minute in total, and methyl alcohol at a rate of 0.03 g per minute (about 3 times by mol of the stoichiometrically required amount) were continuously fed into a stainless pipe having a diameter of 4.9 mm and a length of 250 mm in which 9.9 g of calcium oxide (CaO) molded into a grain of an about 1 mm was filled and fixed (liquid space velocity: 1.3/h, calculated as triglyceride). The reaction temperature was kept at 280° C., and the reaction pressure was controlled to 6 MPa with an outlet control valve (the alcohol being in a subcritical state). The reaction product obtained after three hours from the beginning of the reaction was separated by centrifugation into an oily layer and a glycerol layer. The ratio of methyl ester of a fatty acid generated in the oily layer was analyzed by gas chromatography. As a result, the ratio was 98%.

Example 2-2

A reaction was carried out under the same conditions except that magnesium oxide (MgO) molded into a grain of about 1 mm was used. The ratio of methyl ester of a fatty acid generated after 3 hours was 98%.

Example 2-3

A reaction was carried out under the same conditions as in Example 2-1 except that magnesium oxide (MgO) molded into a grain of about 1 mm was used, and that unrefined palm oil having an acid value of 6 was used as a raw material oil. Samples were taken from the reaction mixture after 3 hours and after 6 hours from the beginning of the reaction, and the ratios of methyl ester of a fatty acid generated of the samples were determined in the same manner as in Example 2-1. The ratio generated after 3 hours was 94%, and the ratio generated after 6 hours was 96%.

Comparative Example 2-1

A reaction was carried out under the same conditions as in Example 2-1 except that the catalyst was not filled. The ratio of methyl ester of a fatty acid generated after 3 hours was 48%.

Comparative Example 2-2

A reaction was carried out under the same conditions as in Comparative Example 2-1 except that the reaction temperature was 340° C. and the reaction pressure was 9 MPa (the alcohol being in a supercritical state). The ratio of methyl ester of a fatty acid generated after 3 hours was 32%.

Comparative Example 2-3

A reaction was carried out under the same conditions as in Example 2-1 except that the reaction temperature was 150° C. and the reaction pressure was 0.9 MPa (the alcohol being in neither a supercritical nor a subcritical state), and that MgO was used as the catalyst. The ratio of methyl ester of a fatty acid generated after 3 hours was 5%.

Comparative Example 2-4

A reaction was carried out under the same conditions as in Example 2-1 except that a commercially available sodium hydroxide pellet (grain of about 5 mm) was used as the catalyst. As a result, the catalyst was dissolved, so that an oily layer containing an ester and a glycerol layer were emulsified, thereby making it difficult to separate into the layers.

It can be seen from Examples 2-1 to -3 that according to the process for preparing an alkyl ester of a fatty acid of the present invention, the methyl ester of a fatty acid can be efficiently prepared. On the other hand, it can be seen from Comparative Examples 2-1 and -2 that when the catalyst of the present invention is not used, the preparation efficiency for the methyl ester of a fatty acid is dramatically lowered even if the reaction temperature and the reaction pressure were increased. It can be seen from Comparative Example 2-3 that when the alcohol is neither in a supercritical state nor in a subcritical state, the preparation efficiency for the methyl ester of a fatty acid is dramatically lowered even if the catalyst of the present invention were used. Also, it can be seen from Comparative Example 2-4 that when the alcohol is in a supercritical or subcritical state and an alkali metal catalyst is used as a catalyst, the methyl ester of a fatty acid cannot be easily separated, so that the preparation efficiency for the methyl ester of a fatty acid is dramatically lowered. In other words, it can be seen that even if any one of the required elements of the present invention were lacking, the preparation efficiency for the methyl ester of a fatty acid is dramatically lowered.

INDUSTRIAL APPLICABILITY

According to the present invention, the alkyl ester of a fatty acid which can be effectively utilized as a diesel fuel oil or the like can be prepared at high efficiency and on an industrial scale from a fat or oil, especially triglyceride mainly contained in a waste oil. In the process for preparing the alkyl ester of a fatty acid of the present invention, the step of separating and collecting a catalyst, or in addition to such a step a pretreatment step for removal of a free fatty acid contained in a fat or oil and an after-treatment step for removal of fatty acid soap can be simplified or omitted. Therefore, according to the process, the productivity for the alkyl ester of a fatty acid is remarkably improved as compared to those of conventional processes.

What is claimed is:

1. A process for preparing an alkyl ester of a fatty acid characterized by a use of a catalyst comprising a composite metal oxide having a perovskite structure in the preparation of the alkyl ester of a fatty acid by a transesterification reaction between a fat or oil and an alcohol in the presence of the catalyst.

2. The process according to claim 1, wherein the composite metal oxide comprises at least one member selected from the group consisting of Ca, St and Ba.

3. The process according to claim 1 or 2, wherein the catalyst further comprises a cesium compound in an amount of from 1 to 10% by mass as calculated by the mass of cesium.

4. The process of claim 1, wherein the transesterification reaction is carried out by using a fixed bed, flow-type reactor in which a solid catalyst formed by molding the catalyst is filled and fixed.

5. A process for preparing an alkyl ester of a fatty acid characterized in that in the preparation of the alkyl ester of a fatty acid by transesterification reaction between a fat or oil and an alcohol in the presence of a catalyst, the alcohol is made into a supercritical state or subcritical state, and at least one member selected from the group consisting of oxides, hydroxides, and carbonates of alkaline earth metals is used as the catalyst.

6. The process according to claim 5, wherein the alkaline earth metal is magnesium.

7. The process according to claim 5 or 6, wherein the transesterification reaction is carried out by using a fixed bed, flow-type reactor in which a solid catalyst formed by molding the catalyst is filled and fixed.

8. The process according to claim 4, wherein a feed amount of the fat or oil is from 1 to 30/h in terms of the liquid space velocity calculated as a triglyceride.

9. The process according to claim 1, wherein the alcohol is an alcohol having a saturated, linear or branched hydrocarbon backbone having 1 to 8 carbon atoms.

* * * * *